United States Patent
Provost et al.

(10) Patent No.: US 7,283,153 B2
(45) Date of Patent: Oct. 16, 2007

(54) HOME-BASED REMOTE MEDICAL ASSISTANCE

(75) Inventors: Hervé Provost, Seyssinet-Pariset (FR); Marc Berenguer, Revel (FR)

(73) Assignee: France Telecom, Paris (FR)

( * ) Notice: Subject to any disclaimer, the term of this patent is extended or adjusted under 35 U.S.C. 154(b) by 607 days.

(21) Appl. No.: 10/221,695

(22) PCT Filed: Mar. 8, 2001

(86) PCT No.: PCT/FR01/00692

§ 371 (c)(1),
(2), (4) Date: Jan. 27, 2003

(87) PCT Pub. No.: WO01/69906

PCT Pub. Date: Sep. 20, 2001

(65) Prior Publication Data
US 2003/0179292 A1    Sep. 25, 2003

(30) Foreign Application Priority Data
Mar. 16, 2000    (FR) ................................. 00 03367

(51) Int. Cl.
*H04N 7/14* (2006.01)
(52) U.S. Cl. ................. 348/14.01; 348/14.03; 379/106.02
(58) Field of Classification Search .. 348/14.01–14.09; 379/38, 106.02, 102.01; 600/300; 417/63; 340/573.1, 3.31, 3.32
See application file for complete search history.

(56) References Cited

U.S. PATENT DOCUMENTS

| | | | | |
|---|---|---|---|---|
| 5,544,649 A | | 8/1996 | David et al. | |
| 5,694,452 A | * | 12/1997 | Bertolet | 379/51 |
| 6,024,539 A | * | 2/2000 | Blomquist | 417/63 |
| 6,219,408 B1 | * | 4/2001 | Kurth | 379/106.02 |
| 6,406,426 B1 | * | 6/2002 | Reuss et al. | 600/300 |

FOREIGN PATENT DOCUMENTS

| | | | |
|---|---|---|---|
| EP | 857456 A1 | * | 8/1998 |
| JP | 2000-036091 | * | 2/2000 |
| WO | WO/9840009 | | 9/1998 |

* cited by examiner

*Primary Examiner*—Melur Ramakrishnaiah
(74) *Attorney, Agent, or Firm*—Cohen Pontani Lieberman & Pavane LLP

(57) ABSTRACT

A system for providing a patient with remote medical assistance at home a patient station (100) includes at least a remotely controllable patient video camera (101) and a patient computer (110) provided with means (111) for acquiring data from medical assistance appliances (11, 12), with relay means (112) for forwarding commands to the appliances, and with means (113) for connection to a telecommunications network (3). A carer station (200) includes, at least a display screen (202) suitable for receiving images from the patient video camera (101), and a carer computer (200) provided with means (213) for connection to the telecommunications network (3) in order to set up a call with the patient station (100), means (211) for remotely controlling the patient station, suitable for remotely controlling the patient video camera (101) and for sending the commands to the patient computer (110), and means (212) for use after remote control for monitoring and feedback purposes by displaying on the display screen (202) images supplied by the patient camera (101) and by transferring to the carer computer (210) data that has been transmitted from the acquisition means (111) of the patient computer via the telecommunications network (3). The system is applicable to enabling patients to be cared for at home.

14 Claims, 3 Drawing Sheets

HOME-BASED REMOTE MEDICAL ASSISTANCE

This application is a U.S. National Phase Application under 35 USC 371 of International Application PCT/FR01/00692 filed 08 Mar. 2001.

FIELD OF THE INVENTION

The present invention relates to a system for providing a patient with remote medical assistance at home.

A particularly advantageous application of the invention lies in all fields of providing medical assistance at home, whether enabling patients to remain at home, providing them with nursing care at home, or providing them with home hospitalization, and more generally it applies to any means that enable patients living in their usual surroundings to benefit from medical assistance and surveillance.

This applies in particular to patients suffering from diseases that require regular medical monitoring, using dedicated medical assistance appliances while not staying in a hospital. Such care can require, for example, the use of oxygen concentrators in oxygen Medical assistance appliances 11, 12 are installed at the patient's home 1, together with a patient computer 110 having means 111 for acquiring data coming from said appliances 11, 12. therapy, the use of food pumps, the use of chemotherapy pumps, and the use of sensors suitable for generating warnings or alarms concerning the state of the patient, or concerning the state of appliances beside the patient.

BACKGROUND OF THE INVENTION

Systems are known for monitoring compliance with a particular treatment, e.g. oxygen therapy, by reporting data measured on medical appliances to a remote point. Other systems provide the option of remotely programming the equipment. Still other equipment is suitable for sending warnings or alarms concerning the state of the patient and/or the state of appliances in the vicinity to the patient, which equipment includes remote alarm systems that are triggered by voluntary action of the patient or in response to an event generated by a sensor.

Nevertheless, those known systems do not inspire carers with much confidence about what is actually taking place at the patient's home.

For systems that report measured data to a remote point, the carer is informed only after the event that treatment has not been properly complied with, and being at a distance, the carer has little means for guiding and/or educating the patient towards better compliance.

In systems that enable appliances to be remotely programmed, only certain items of data are returned in the guise of an acknowledgment of receipt in response to remote programming. If a display is provided on the remote appliance, then the patient can use the telephone to corroborate that a change of state of the appliance has taken place. Nevertheless, even with such corroboration, the carer cannot ensure that the installation is functioning properly overall (and in particular cannot inspect the tubing).

Finally, conventional alarm or warning systems do not enable action to be taken remotely on the cause of an alarm or warning, and, in the absence of further information, a carer having any doubts concerning the validity of the alarm or warning or concerning the state of the patient will have to make a visit.

One object of the present invention is to provide a system for rendering remote medical assistance to a patient at home that makes it possible in particular to guarantee that the real operation of the appliances in the vicinity of the patient does indeed comply with the expected operation thereof, to control appliances remotely in order to be able to modify their operating parameters so as to adapt them to the patient's needs, and to give the carer a maximum degree of reassurance and confidence concerning the action taken remotely.

This and other objects are attained in accordance with one aspect of the present invention directed to a patient station comprising at least a remotely controllable patient video camera and a patient computer provided with means for acquiring data from medical assistance appliances, with relaying means for forwarding commands to said appliances, and with means for connection to a telecommunications network; and a carer station comprising at least a display screen suitable for receiving images from said patient video camera, and a carer computer provided with means for connection to said telecommunications network in order to set up a call with the patient station, means for remotely controlling the patient station, suitable for remotely controlling the patient video camera and for sending said commands to the patient computer, and means, for use after remote control operations have been carried out, for monitoring and feedback purposes by displaying on said display screen images supplied by the patient camera and by transferring to the carer computer data that has been transmitted from the acquisition means of the patient computer via the telecommunications network.

Thus, the remote assistance system of the invention makes it possible remotely to monitor the operation of appliances in the patient's home, both visually by means of the patient's video camera to ensure that the patient installation is in its proper state overall, and in particular that the tubing is properly installed, or to read the information provided by displays, and also by transferring data from the acquisition means of the patient computer to the carer computer. Furthermore, it is possible for the carer to modify the operation of the appliances by sending commands via the remote control means of the carer computer and the transmission means of the patient computer. Similarly, in order to enable conversation to be established between the patient and the carer, the patient station and the carer station both include sound communication means. These dispositions have the advantage of putting the two people concerned who are distant from each other into conditions of dialog that are of particular importance for the well-being of the patient.

Two modes of establishing communication between the patient station and the carer station are envisaged. In a first mode, the patient can set up a call with the carer station voluntarily, while in a second mode, a call to the carer station is triggered by an alarm concerning a departure from expected operation or a breakdown of one of said medical assistance appliances.

Another advantageous characteristic of the remote assistance system of the invention concerns the situation of operation under downgraded conditions in which the patient station finds it impossible to set up a call to the carer station, for example outside the opening hours of a home hospitalization service. Under such circumstances, the invention provides for said system further to comprise a relay center suitable for entering into sound communication with a voice generator at the patient's home.

BRIEF DESCRIPTION OF THE DRAWINGS

The following description made with reference to the accompanying drawings given as non-limiting examples makes it easy to understand what the invention consists in and how it can be implemented.

DETAILED DESCRIPTION OF THE DRAWINGS

Figure 1:
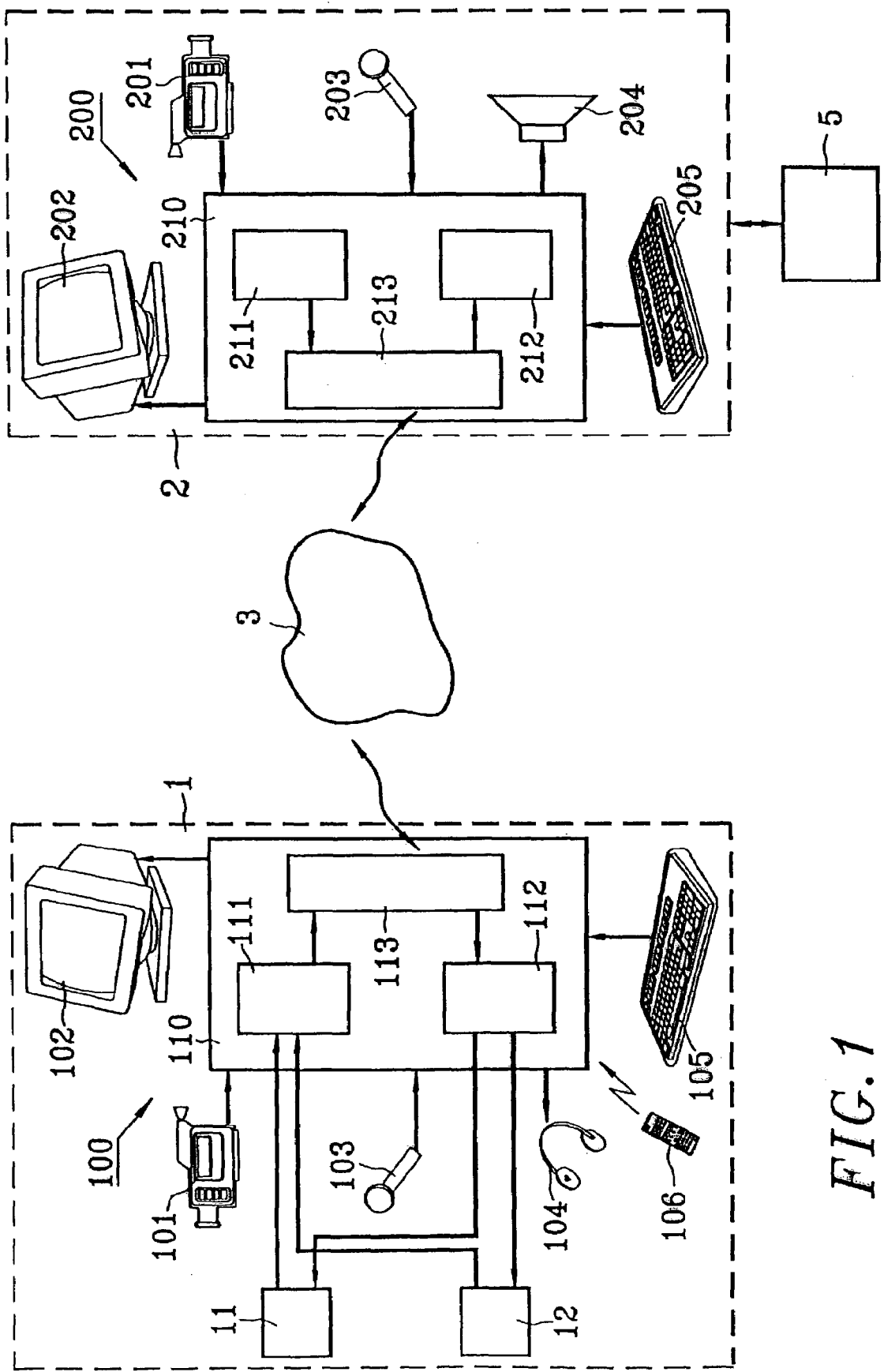
FIG. 1 is a diagram of a patient station and a carer station in a system for remote medical assistance at home in accordance with the invention.

FIG. 1 shows a system for remote medical assistance between the home 1 of a patient and a care center 2, e.g. a hospital service. Essentially, means 111 comprises a memory that receives signals, generally, voltages, delivered by measurement sensors placed on the appliance and relayed via an analog-to-digital converter. Inversely, means 112 for relaying commands is provided to enable the operating parameters of the appliances 11 and 12 to be modified. Naturally, these relaying means 112 can make use of an analog-to-digital converter just like or the same as in the acquisition means 111. Finally, means 113, such as a modem, serve to connect the patient computer 110 to a carer station 200 via a telecommunications network 3, for example the integrated services digital network (ISDN) operating at 128 kilobits per second (Kbits/s).

In FIG. 1, there can also be seen at the patient's home 1 a remotely controllable patient video camera 101, a display screen 102 for receiving images coming from the carer station 200, and sound communication means constituted by a microphone 103, which is possibly a remotely controllable microphone, and playback means, preferably a wireless headphone set 104, for ensuring that the speech received from the carer station 200 remains confidential.

Optionally, the patient computer 110 can be provided with a conventional wired keyboard (not shown), a virtual keyboard on the screen 102, a graphics tablet (not shown), or indeed a wireless keyboard 105, so as to be able to accommodate patients having difficulty in speaking, e.g. after a tracheotomy.

Finally, the patient station 100 can be activated by a remote control 106 to enable the patient to initiate a call to the carer station 200, to answer when a carer calls, or to interrupt an on-going conversation.

As shown in FIG. 1, the carer station 200 comprises a display screen 202 suitable for receiving images coming from the patient video camera 101, a carer video camera 201 for supplying the patient display screen 102 with images, essentially images of the carer, and sound communication means, specifically a microphone 203 and a loudspeaker 204.

A carer computer 210 is provided with means, e.g. a modem 213, for connection to the telecommunications network 3 in order to set up a call with the patient station 100. The computer 210 has remote control means 211 serving in general terms to enable the carer to act on the entire installation situated at the patient's home, and more particularly to act on the means that provide information concerning the state of the patient and the operation of the medical assistance appliances 11, 12. Thus, said remote control means 211 are suitable both for remotely panning, tilting and zooming the patient video camera 101 by means of a joystick so as to enable the carer to examine the patient visually or to inspect the appliances, and also to send commands to the patient computer 110 to be relayed via the relaying means 112 to the appliances 11, 12.

After the remote control operations are carried out, monitoring or feedback means 212 enable the carer to verify that the real state of the patient installation complies with the desired state. Monitoring can be performed by causing images from the patient video camera 101 to be displayed on the screen 202 and/or by causing data to be transferred from the acquisition means 111 of the patient computer 110 via the telecommunications network 3.

Finally, the carer station 200 can be connected to input means (e.g. a scanner, a digital camera, etc.-not shown) for receiving information for local use or for transmission to the patient station 100. In this way, a carer can send a prescription, for example, or the results of analyses to a doctor present at the patient's home.

Medical assistance appliances 11, 12 are installed at the patient's home 1, together with a patient computer 110 having means 111 for acquiring data coming from said appliances 11, 12.

It should be observed that by default the stations 100 and 200 are configured for point-to-point communication, i.e. in pairs. Under such circumstances, the patient always communicates with the same carer station. However, it is also possible for a call coming from the patient to be switched manually or automatically to an available carer station in a given corresponding hospital service. In contrast, a given carer can communicate with each of the patients in his or her care. Nevertheless, it is possible to envisage that a patient station can also communicate with carer stations other than the station designated by default. For example, a patient may communicate with a nursing service by default but can also communicate with the doctor in charge who has the same kind of station as the nursing service.

Furthermore, depending on the particular communications network 3 that is used, it can be possible to handle multipoint calls between stations, e.g. by using ISDN bridges or Internet protocol (IP) reflectors. This applies to combined action taken by a carer of a nursing service, the patient's doctor, and the patient.

FIG. 1 shows that the carer station 200 is connected to an auxiliary telephone set 5 which might be several meters away, in order to enable a secretary to receive sound calls coming from the patient station 100.

Figure 2:
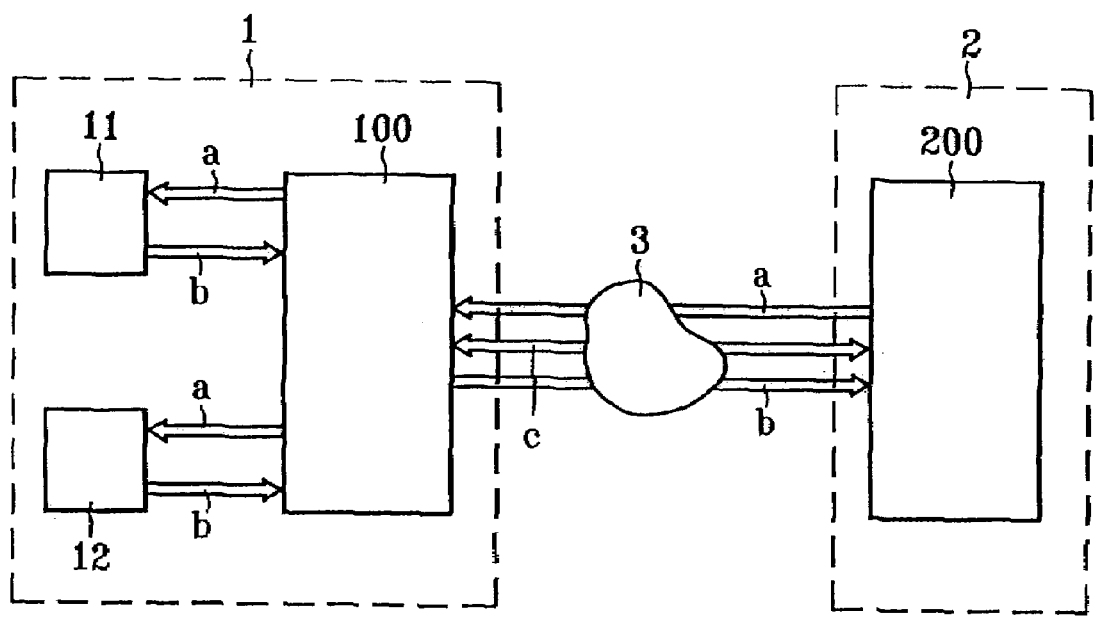
FIG. 2 is a block diagram showing the operation of the FIG. 1 system during a call between the stations.

The general operation of the remote assistance system of FIG. 1 is illustrated by the diagram of FIG. 2.

Depending on the needs of the patient, the doctor will have prescribed some particular treatment which is administered in this case by using the medical remote assistance appliances 11 and 12: e.g. a food pump, a morphine pump, or an oxygen concentrator. These appliances are programmed accordingly and they are capable of operating independently. In addition to this local control, each of the appliances is organized to receive remote control commands by putting a patient station 100 installed in the patient's home 1 into communication with a carer station 200 situated in the care center 2.

With the appliances 11, 12 ready to operate or already operating in the patient's home 1, the carer can send commands (arrows a in F*igure* 2) remotely to said appliances via the remote control means 211 of the carer computer 210 and the relaying means 112 of the patient computer 110. The carer can also monitor the appliances or obtain feedback concerning the effects of commands that have been issued (arrows b in Figure 2), either by looking at the screen 202 to read values, measurements, or acknowledgments of receipt as delivered electronically by the acquisition means 111 of the patient station 100, or by looking directly at the appliances by remotely controlling the patient video camera 101. Then, depending on the appliance, it is possible to read its display or to become aware of any indication that can be derived by observing the appliance in operation. By using the camera 101, the carer can also monitor overall operation of the installation (inspecting the tubing, etc.) and/or can engage in a video telephone conversation with the patient (arrow c in Figure 2) and observe the patient's reactions, talking to the patient while the appliances are carrying out their actions.

It should also be observed that in addition to issuing direct commands to the appliances, it is possible for the carer to issue parameters for a program running on the patient computer 110 for the purpose of ensuring that medical treatment is administered appropriately over time (e.g. varying gas flow rates when applying oxygen therapy), in the event of it not being possible to program the appliances themselves in satisfactory manner. The computer program is suitable for receiving parameters remotely from the carer station 200 or locally on the occasion of a visit.

Figure 3:
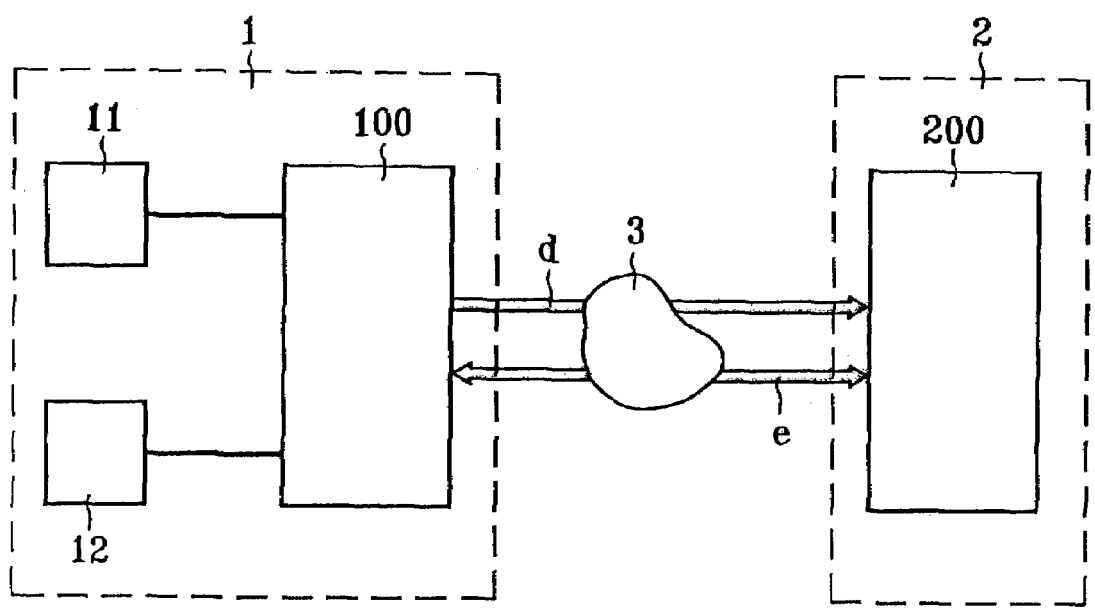
FIG. 3 is a block diagram showing the operation of the FIG. 1 system when an alarm is triggered at the patient's home.

A call can also be made at the initiative of the patient station 100, either under voluntary control of a patient seeking to make contact with the carer for any reason whatsoever, or in the event of a warning or an alarm. This second possibility is described below with reference to FIG. 3.

While no video phone call is set up between the patient and the carer, the patient station 100 continues to monitor the operation of the medical appliances 11, 12 in autonomous manner. Thus, if an alarm is triggered because operation departs from expected operation, or because of a breakdown or a warning involving an appliance, e.g. 11, or in the event of the appliance 11 being incapable of administering the treatment as initially programmed (supply exhausted, tubing obstructed, etc.), the patient station 100 sets up a call with the carer station 200 which, depending on carer preferences, can consist in sending a warning/alarm message (arrow d in FIG. 3) with an indication of the reasons for the warning/alarm, or in triggering a video phone call (arrow e in FIG. 3), overriding any voluntary call from the patient, with the reason for the call being displayed at the carer end.

Once a call has been set up, the carer takes a look at the patient's surroundings and depending on circumstances can:

issue new commands to the appliance 11 including, where possible, switching off any persistent alarm bells;

guide someone present at the patient's home 1 in remedying the alarm, for example removing a fallen object that is obstructing tubing, purging a bubble from the tubing, . . . ; or provide the patient and any one else present with support while waiting for competent personnel to arrive.

Figure 4:
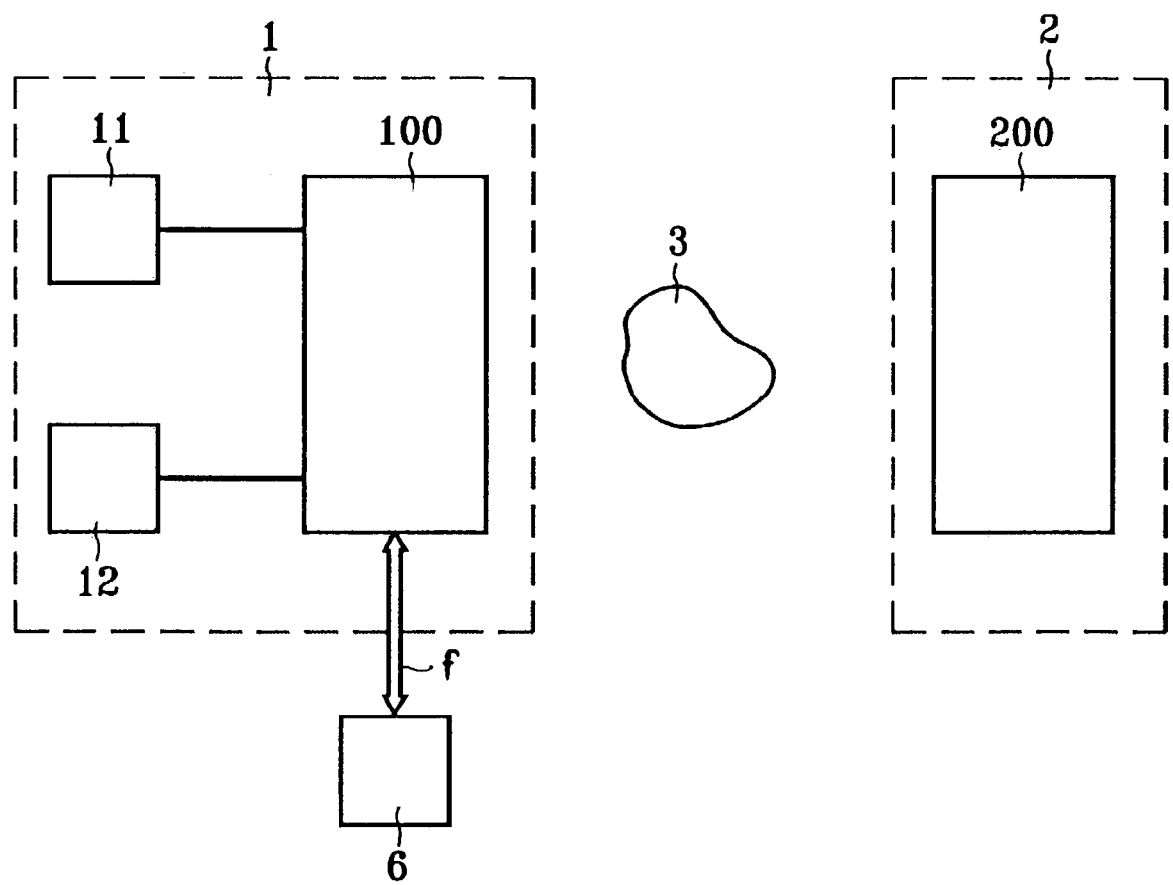
FIG. 4 is a diagram showing how the FIG. 1 system operates under downgraded conditions.

FIG. 4 shows how the system of the invention takes account of operation under downgraded conditions.

Conditions are downgraded when the patient station 100 cannot set up a call with the carer station 200, for example after operating hours at the home hospitalization service have ended. Under such circumstances, in order to ensure care continuity, the patient station 100 initiates a sound call with a replay center 6 (arrow f in FIG. 4), which center does not have any station equipment but merely has a telephone set. The relay center 6 is generally an emergency medical service.

The reason for the warning or the alarm is given to the carer at the relay center 6 by means of a voice generator. The carer can optionally enter into communication with the patient by pressing on a special key on the telephone set after receiving information from said voice generator.

The invention claimed is:

1. A system for providing remote medical assistance to a patient at home, comprising:
    (a) a patient station comprising
        a remotely controllable patient video camera for supplying at least one of images of medical assistance appliances and images of a patient; and
        a patient computer provided with
            (i) means for acquiring data from said appliances;
            (ii) relaying means for forwarding commands to said appliances for modifying operating parameters of said appliances; and
            (iii) means for connection to a telecommunications network; and
    (b) a carer station comprising
        a display screen suitable for receiving images from said patient video camera; and
        a carer computer provided with
            (i) means for connection to said telecommunications network in order to set up a communication with the patient station;
            (ii) means for remotely controlling the patient station, suitable for remotely controlling the patient video camera and for sending said commands to the patient computer;
        and
            (iii) means for monitoring said appliances and obtaining feedback concerning effects of said commands after remote control operations have been carried out, by displaying on said display screen images of said appliances supplied by the patient video camera and by displaying said data after transmission via the telecommunication network from said aquisition means to the carer computer.

2. The remote assistance system according to claim 1, wherein the patient station also has a display screen suitable for receiving images from a carer video camera situated at the carer station.

3. The remote assistance system according to claim 1, wherein the patient station and the carer station include means for sound communication.

4. The remote assistance system according to claim 3, wherein the sound communication means of the patient station comprise a microphone that is remotely controlled by the remote control means of the carer station.

5. The remote assistance system according to claim 3, wherein the sound communication means of the patient station include a wireless audio headset.

6. The remote assistance system according to claim 1, wherein said system further comprises a relay center suitable for entering into sound communication with a voice generator at the patient's home.

7. The remote assistance system according to claim 1, wherein the carer station is connected to means for inputting data for local use or for transmission to the patient station from the carer computer via the telecommunications network.

8. The remote assistance system according to claim 1, wherein the carer station is connected to auxiliary telephone equipment for receiving sound calls from the patient station.

9. The remote assistance system according to claim 1, wherein the patient station can be activated by a remote control unit.

10. The remote assistance system according to claim 1, wherein the patient computer is provided with a wired keyboard, a virtual keyboard on the display screen, a graphics tablet, or with a wireless keyboard.

11. The remote assistance system according to claim 1, wherein a call with the carer station can be set up voluntarily by the patient.

12. The remote assistance system according to claim 1, wherein a call with the carer station can be triggered by an alarm in the event of operation departing from expected operation, in the event of a breakdown, or in the event of a warning from one of said medical assistance appliances.

13. A patient station of a system for remote medical assistance of a patient at home, wherein the station comprises:

a remotely controllable patient video camera for supplying at least one of images of medical assistance appliances and images of a patient; and a patient computer provided with
   (i) means for connection to a telecommunications network;
   (ii) means for acquiring data from said appliances and for transmitting via the telecommunications network said data to a carer computer; and
   (iii) means for forwarding commands to said appliances for modifying operating parameters of said appliances, said commands being sent from remote control means of said carer computer.

14. A carer station of a system for remote medical assistance of a patient at home, wherein the station comprises:

a display screen suitable for receiving images from a patient video camera; and a carer computer provided with
   (i) means for connection to a telecommunications network in order to set up a communication with a patient station;
   (ii) means for remotely controlling the patient station, suitable for remotely controlling a patient video camera and for sending commands for modifying operating parameters of medical assistance appliances to a patient computer; and
   (iii) means for monitoring said appliances and obtaining feedback concerning effects of said commands after remote control operations have been carried out, by displaying on said display screen images of said appliances supplied by the patient video camera and by displaying data after transmission via the telecommunications network from said acquisition means to the carer computer.

* * * * *